(12) United States Patent
Pullagurla et al.

(10) Patent No.: US 10,723,745 B2
(45) Date of Patent: Jul. 28, 2020

(54) ISOSULFAN BLUE, ITS CRYSTALLINE FORM AND PROCESS FOR PREPARATION THEREOF

(71) Applicant: BIOPHORE INDIA PHARMACEUTICALS PVT. LTD., Hyderabad (IN)

(72) Inventors: Manik Reddy Pullagurla, Hyderabad (IN); Mecheril Valsan Nanda Kumar, Hyderabad (IN); Bhaskar Reddy Pitta, Hyderabad (IN); Suresh Babu Namana, Hyderabad (IN); Jagadeesh Babu Rangisetty, Hyderabad (IN); Sadashiv Choppari, Hyderabad (IN)

(73) Assignee: BIOPHORE INDIA PHARMACEUTICALS PVT. LTD., Hyderabad (IN)

( * ) Notice: Subject to any disclaimer, the term of this patent is extended or adjusted under 35 U.S.C. 154(b) by 0 days.

(21) Appl. No.: 16/315,270

(22) PCT Filed: Sep. 6, 2016

(86) PCT No.: PCT/IN2016/050297
§ 371 (c)(1),
(2) Date: Jan. 4, 2019

(87) PCT Pub. No.: WO2018/008040
PCT Pub. Date: Jan. 11, 2018

(65) Prior Publication Data
US 2019/0225626 A1    Jul. 25, 2019

(30) Foreign Application Priority Data
Jul. 6, 2016  (IN) .............................. 201641023263

(51) Int. Cl.
*C07C 303/00* (2006.01)
*C07F 1/04* (2006.01)
(Continued)

(52) U.S. Cl.
CPC .............. *C07F 1/04* (2013.01); *C07C 303/00* (2013.01); *C07C 303/04* (2013.01);
(Continued)

(58) Field of Classification Search
CPC ... C07C 309/44; C07C 309/46; C07C 303/04; C07C 303/06; C07C 303/22; C07C 303/44; C07C 303/00; C07B 2200/13; C07F 1/04
See application file for complete search history.

(56) References Cited

U.S. PATENT DOCUMENTS

| 1,531,507 A | 3/1925 | Rosenbaum |
| 2006/0224003 A1* | 10/2006 | Kulkarni .................. C09B 11/14 552/111 |

(Continued)

FOREIGN PATENT DOCUMENTS

| IN | 03879/MUM/2014 | 6/2016 |
| IN | 263/CHE/2014 | 7/2016 |

OTHER PUBLICATIONS

IN201621000866 (Year: 2016).*
(Continued)

*Primary Examiner* — Jafar F Parsa
*Assistant Examiner* — Blaine G Doletski
(74) *Attorney, Agent, or Firm* — Schmeiser, Olsen & Watts, LLP (57) ABSTRACT

Provided is an improved process for the preparation N-[4-[[4-(diethyl amino) phenyl](2,5-disulfophenyl)methylene]-2,5-cyclohexadien-1-ylidene]-N-ethylethanaminium inner salt sodium salt (Isosulfan blue) of formula I. It also relates to highly pure novel crystalline form of Isosulfan blue hydrate and its process for the preparation thereof. It also relates to an improved process for the preparation of Isosulfan blue sodium hydrate having not more than 0.2% of desethyl impurity of formula A.

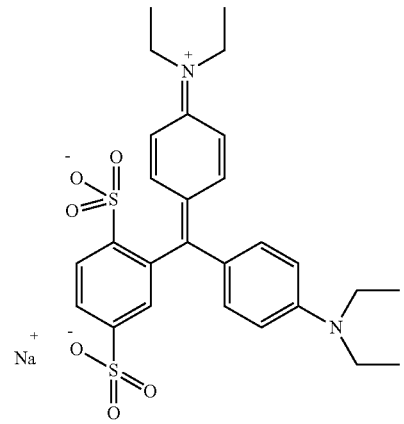

Formula I

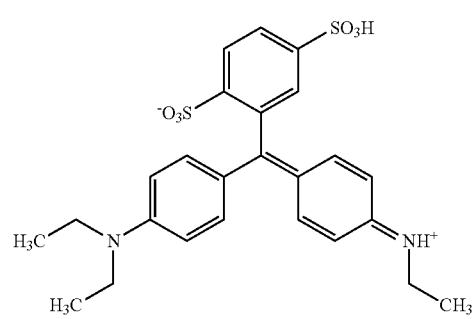

Formula A

3 Claims, 3 Drawing Sheets (51) Int. Cl.
    *C07C 303/04*      (2006.01)
    *C07C 303/44*      (2006.01)
    *C07C 303/22*      (2006.01)
    *C07C 303/06*      (2006.01)

(52) U.S. Cl.
    CPC .......... *C07C 303/06* (2013.01); *C07C 303/22* (2013.01); *C07C 303/44* (2013.01); *C07B 2200/13* (2013.01)

(56) References Cited

U.S. PATENT DOCUMENTS

| | | | |
|---|---|---|---|
| 2013/0310600 A1 | 11/2013 | Kovi et al. | |
| 2019/0010330 A1* | 1/2019 | Vyas | C09B 11/18 |
| 2019/0152903 A1* | 5/2019 | Ramanathan | C07C 303/06 |

OTHER PUBLICATIONS 62351018 (Year: 2016).*
International Search Report; PCT/IN2016/050297; International Filing Date: Sep. 6, 2014.
Written Opinion; PCT/IN2016/050297; International Filing Date: Sep.6, 2014.

* cited by examiner

Figure 1: XRPD peaks pattern of Isosulfan blue (I) hydrate

Figure 2: TGA thermogram of crystalline form of Isosulfan blue (I) hydrate

Figure 3: HPLC chromatogram of desethyl impurity of formula A

US 10,723,745 B2

ISOSULFAN BLUE, ITS CRYSTALLINE FORM AND PROCESS FOR PREPARATION THEREOF

CROSS-REFERENCE TO RELATED APPLICATIONS

This application claims priority to PCT Application No. PCT/IN2016/050297, having a filing date of Sep. 6, 2016, based on IN 201641023263, having a filing date of Jul. 6, 2016, the entire both contents of which are hereby incorporated by reference.

FIELD OF TECHNOLOGY

The following relates to an improved process for the preparation of Isosulfan blue. More particularly, the following relates to highly pure crystalline form of Isosulfan blue (I) hydrate and its process for the preparation thereof. The following also relates to an improved process for the preparation of Isosulfan blue sodium hydrate having not more than 0.2% of desethyl impurity of formula A.

BACKGROUND

The compound N-[4-[[4-(diethyl amino) phenyl](2,5-disulfophenyl)methylene]-2,5-cyclohexadien-1-ylidene]-N-ethylethanaminium inner salt sodium salt (Isosulfan blue) is represented by the formula (I)

Formula I

Isosulfan blue (I) is a triarylmethane dye used as a contrast agent for delineation of lymphatic vessels and is particularly useful as a cancer diagnostic agent. Isosulfan blue is marketing as lymphazurin blue dye, which is available as 1% (10 mg/ml) 5 ml solution for injection.

U.S. Pat. Nos. 1,531,507, 7,534,911, 8,969,616 reported various processes for the synthesis of dyes specifically, Isosulfan blue, the contents of which are hereby incorporated as reference in their entirety.

General synthesis of Isosulfan blue was first described in the U.S. Pat. No. 1,531,507. According to this Isosulfan blue is made by converting orthochlorobenzaldehyde to sodium salt of 2-chlorobenzaldehyde-5-sulfonic acid by sulphating using oleum (26% or oleum 65%) and sodium carbonate, which is further treated with sodium sulphite to produce benzaldehyde-2,5-disulfonic acid sodium salt followed by condensation with alkylated aryl amine to produce isoleuco compound. The obtained compound is oxidised to produce Isosulfan blue. The yield and purity of the final compound is not reported in the known art.

U.S. Pat. No. 7,534,911 patent discloses another route for the synthesis of Isosulfan blue (Scheme-1) by sulphonating orthochlorobenzaldehyde with Oleum (23% to 65%) to obtain 2-chlorobenzaldehyde-5-sulfonic acid, which is subsequently treated with sodium sulphite and followed by basification produces sodium salt of benzaldehyde-2,5-disulfonic acid sodium. This is further treated with sodium sulphite to get disodium salt followed by condensation with diethyl aniline to yield sodium 2-(bis(4-(diethylamino)phenyl)methyl)benzene-1,4-disulfonate and oxidizing the obtained compound with ammonium dichromate in presence of sulphuric acid affords Isosulfan blue.

Isosulfan blue
1

U.S. Pat. No. 8,969,616 discloses another route of synthesis of synthesis for Isosulfan blue (Scheme-2). In this Isosulfan blue is obtained by the reaction of 4-Chloro-3-formylbenzenesulfonic acid with sodium sulphite and sodium sulphite mixture in presence of water at very high temperature (180° C.) under high pressure (150 PSI) by isolating the crude with huge volumes of methanol further underwent purifications using huge volumes of Dimethylformamide and Dichloromethane solvent to get pure compound and ends in very low yield to get Sodium-2-formyl-benzene-1,4-disulfonate. Further reaction of Sodium-2-formylbenzene-1,4-disulfonate with diethyl aniline in presence of urea and acetic acid at reflux temperature for longer hours (20-25 hrs) then isolated by cooling the reaction mixture followed by addition of anti-solvent methanol to give crude 2-(Bis(4-(diethylamino)phenyl) methyl)benzene-1,4-disulfonic acid. The isolated crude underwent purifications to give pure 2-(Bis(4-(diethylamino)phenyl) methyl)benzene-1,4-disulfonic acid. The 2-(Bis(4-(diethylamino)phenyl)methyl)benzene-1,4-disulfonic acid gets oxidized in presence of silver oxide in methanol media and further isolation using Diisopropylether to obtain Isosulfan blue.

Therefore, there is a need in the art for an improved method for the preparation of Isosulfan blue in significantly high yield and purity. In view of this, the present inventors provide a safe and cost-effective process for the preparation of Isosulfan blue in significantly high yield.

SUMMARY

An aspect relatest to an improved process for the preparation of Isosulfan blue.

Another aspect of the embodiments of the invention is to provide novel crystalline form of Isosulfan blue hydrate.

Another aspect of the embodiments of the invention is to provide process for preparing crystalline form of Isosulfan blue hydrate containing 4-10% of moisture content.

Another aspect of embodiments of the invention is to provide purification process to remove desethyl impurity of formula A.

Another aspect of embodiments of the invention is to provide Isosulfan blue having desethyl impurity level less than 0.2%.

Another aspect of embodiments of the invention is to provide Isosulfan blue with metal content lead level less than 2 ppm, Arsenic level less than 3 ppm and chromium level less than 50 ppm.

Another aspect of embodiments of the invention is to provide process for preparing pure Isosulfan blue, which is having total impurity level less than 3% and desethyl impurity level less than 0.2% and metal content lead level less than 2 ppm, Arsenic level less than 3 ppm and chromium level less than 50 ppm.

Accordingly, embodiments of the present invention provides improved process for the preparation of N-[4-[[4-(diethyl amino) phenyl](2,5-disulfophenyl)methylene]-2,5-cyclohexadien-1-ylidene]-N-ethylethanaminium inner salt sodium salt (Isosulfan blue) of formula I, which is schematically represented in Scheme-3.

In one aspect, embodiments of the present invention provides a process for the preparation of Isosulfan blue comprises the following steps:

a) sulphonating 2-chloro benzaldehyde compound of formula II with fuming sulphuric acid to obtain 4-chloro-3-formyl-benzenesulfonic acid compound of formula III;

Formula II            Formula III b) treating the 4-Chloro-3-formyl-benzenesulphonic acid compound of formula III obtained in step (a) with alkali metal sulphite to obtain 1-formyl benzene-2,5-disulphonic acid disodium salt of formula IV;

Formula IV c) condensing 1-formyl benzene-2,5-disulphonic acid disodium salt of formula IV obtained in step (b) with N,N-diethylaniline of formula V in presence of hydrochloric acid to obtain 4-[Bis[4-(diethylamino)phenyl]methyl]benzene-2,5-disulphonic acid compound of formula VI;

Formula V

Formula VI d) oxidizing 4-[Bis[4-(diethylamino)phenyl]methyl]benzene-2,5-disulphonic acid of formula VI with an oxidizing agent in presence of sulphuric acid to obtain crude Isosulfan blue of formula VII, and purifying;

Formula VII e) optionally, recrystallizing the Isosulfan blue of formula VII obtained in step (d) to obtain highly pure Isosulfan blue.

The alkali metal sulphite in step (b) is selected from the group comprising of sodium sulphite, potassium sulphite, Iron sulphite, zinc sulphite and copper sulphite. In one embodiment the alkali metal sulphite used is sodium sulphite. The reaction in step (b) is carried out in a solvent selected from ethanol, methanol, propanol, isopropanol and water or mixtures thereof.

The process step (c) further comprises purifying the compound of formula VI by treating with a base and converting into free base to get pure compound VI.

The oxidizing agent in step (d) is selected from potassium dichromate, sodium dichromate, zinc dichromate and pyridinium dichromate. In one embodiment the oxidizing agent used is potassium dichromate.

The crude Isosulfan blue of formula VII in step (d) is purified with a solvent selected from the group comprising of methanol, acetone and dichloromethane or mixture thereof. In one embodiment the crude Isosulfan blue of formula VII in step (d) is purified by column chromatography, wherein the column purification comprises using 100-500 mesh silica gel and selecting a polar aprotic eluent from dichloromethane, acetonitrile, methanol, ethanol and the mixtures thereof. In one embodiment the mess size of Silica gel is selected from 100-200, 200-400, 230-400 and 200-425.

The above said process after column purification further comprises the steps of:
  (a) slurring the obtained Isosulfan blue in acetone; and
  (b) recrystallizing from the mixture of polar protic solvents to obtain highly pure Isosulfan blue;
  wherein the polar protic solvent in step (b) is selected from methanol, ethanol, propanol, isopropyl alcohol and tertiary butyl alcohol or mixture thereof.

In one embodiment the recrystallization in step (e) comprises the steps of:
  a) suspending Isosulfan blue in a solvent;
  b) stirring the solution for 1-2 hrs at 25-30° C.;
  c) filtering the solution mass through 0.2-micron filter at 25-30° C.;
  d) distilling off the filtrate under vacuum below 50° C.;
  e) cooling the crude to 25-30° C. and adding solvents like methanol, Ethanol, Isopropyl alcohol, n-butanol, acetone, diethyl ether, Isopropyl ether at 25-30° C.;
  f) stirring for 2-3 hrs at 25-30° C.;
  g) filtering the solid under vacuum at below 30° C.; and
  h) drying the solid under vacuum below 50° C.;
wherein,
  the solvent in step (a) is selected from the group comprising of methanol, ethanol, isopropanol, n-butanol, acetone, diethyl ether, Isopropyl ether, dichloromethane, acetonitrile, acetic acid, tetrahydrofuran, toluene, ethylacetate and cyclohexane or mixtures thereof;
  the Isosulfan blue obtained from the process is crystalline Isosulfan blue hydrate characterized by X-ray powder diffraction (XRPD) pattern comprising one or more of the reflections at 4.38, 14.64, 15.84, 16.14, 19.49, 22.25, 22.60 and 24.73±0.2 degrees 2 theta (2θ°);
  the Isosulfan blue obtained from the process is crystalline Isosulfan blue hydrate further characterized by X-ray powder diffraction (XRPD) pattern comprising of the reflections at 6.51, 8.80, 11.69, 12.66, 12.90, 13.53, 17.05, 17.68, 18.20, 18.79, 20.29, 21.27, 23.01, 23.92, 25.49, 26.01, 26.78, 27.97, 28.66, 29.29 and 30.58±0.2 degrees 2 theta (2θ°).

The Isosulfan blue obtained from the process comprises a purity level of greater than 99%.

The Isosulfan blue obtained from the process contains moisture content less than 10%.

The Isosulfan blue obtained from the process contains desethyl impurity level less than 0.2%.

The Isosulfan blue obtained from the process contains lead less than 2 ppm, arsenic less than 3 ppm and chromium less than 50 ppm.

The Isosulfan blue obtained from the process contains total organic impurities less than 3% and total metal impurities less than 20 ppm.

In one embodiment the present invention provides a process for the preparation of N-[4-[[4-(diethyl amino)phenyl](2,5-disulfophenyl)methylene]-2,5-cyclohexadien-1-ylidene]-N-ethylethanaminium inner salt sodium salt (Isosulfan Blue) comprising the steps of:

(a) sulphonating 2-Chloro benzaldehyde compound with 1.4 equivalents of 20-25% sulphuric acid (Oleum) at 10-15° C. to obtain 4-Chloro-3-formyl-benzenesulphonic acid;
  (b) converting 4-Chloro-3-formyl-benzenesulphonic acid to 1-formyl benzene-2,5-disulphonic acid disodium salt by treatment with sodium sulphite in presence of water and sodium hydroxide (NaOH) at temperature 85-110° C.;
  (c) condensing 1-formyl benzene-2,5-disulphonic acid disodium salt with N,N-diethyl aniline in presence of hydrochloric acid to obtain 4-[Bis[4-(diethylamino)phenyl]methyl]benzene-2,5-disulphonic acid and optionally purifying;
  (d) oxidizing 4-[Bis[4-(diethylamino)phenyl]methyl]benzene-2,5-disulphonic acid using potassium dichromate in presence of sulphuric acid to obtain crude Isosulfan blue;
  (e) optionally, purifying the crude Isosulfan blue obtained in step (d) by Column chromatography using dichloromethane and methanol to obtain pure Isosulfan blue; and
  (f) optionally, recrystallizing Isosulfan blue obtained in step (d) or step (e) with methanol and Isopropyl alcohol to provide highly pure Isosulfan blue.

In one embodiment, the present invention provides an Isosulfan blue compound of formula-I comprising less than 0.2% of desethyl impurity of the formula A.

In one embodiment, the present invention provides an Isosulfan blue compound of formula-I containing metal impurities comprising lead less than 2 ppm, Arsenic less than 3 ppm and chromium less than 50 ppm.

In one embodiment, the present invention provides an Isosulfan blue compound of formula-I having moisture content less than 10%.

In one embodiment, the present invention provides an Isosulfan blue compound comprising desethyl impurity less than 0.2% and moisture content 4-10%.

In one embodiment, the present invention provides Crystalline Isosulfan blue hydrate characterized by X-ray powder diffraction (XRPD) pattern comprising one or more of the reflections at 4.38, 14.64, 15.84, 16.14, 19.49, 22.25, 22.60 and 24.73±0.2 degrees 2 theta (2θ°).

The above said crystalline Isosulfan blue hydrate is further characterized by X-ray powder diffraction (XRPD)

high yield and substantially pure form. The following is schematically represented in Scheme-3 as follows:

Scheme-3 pattern comprising of the reflections at 6.51, 8.80, 11.69, 12.66, 12.90, 13.53, 17.05, 17.68, 18.20, 18.79, 20.29, 21.27, 23.01, 23.92, 25.49, 26.01, 26.78, 27.97, 28.66, 29.29 and 30.58±0.2 degrees 2 theta (2θ°).

Figure 1:
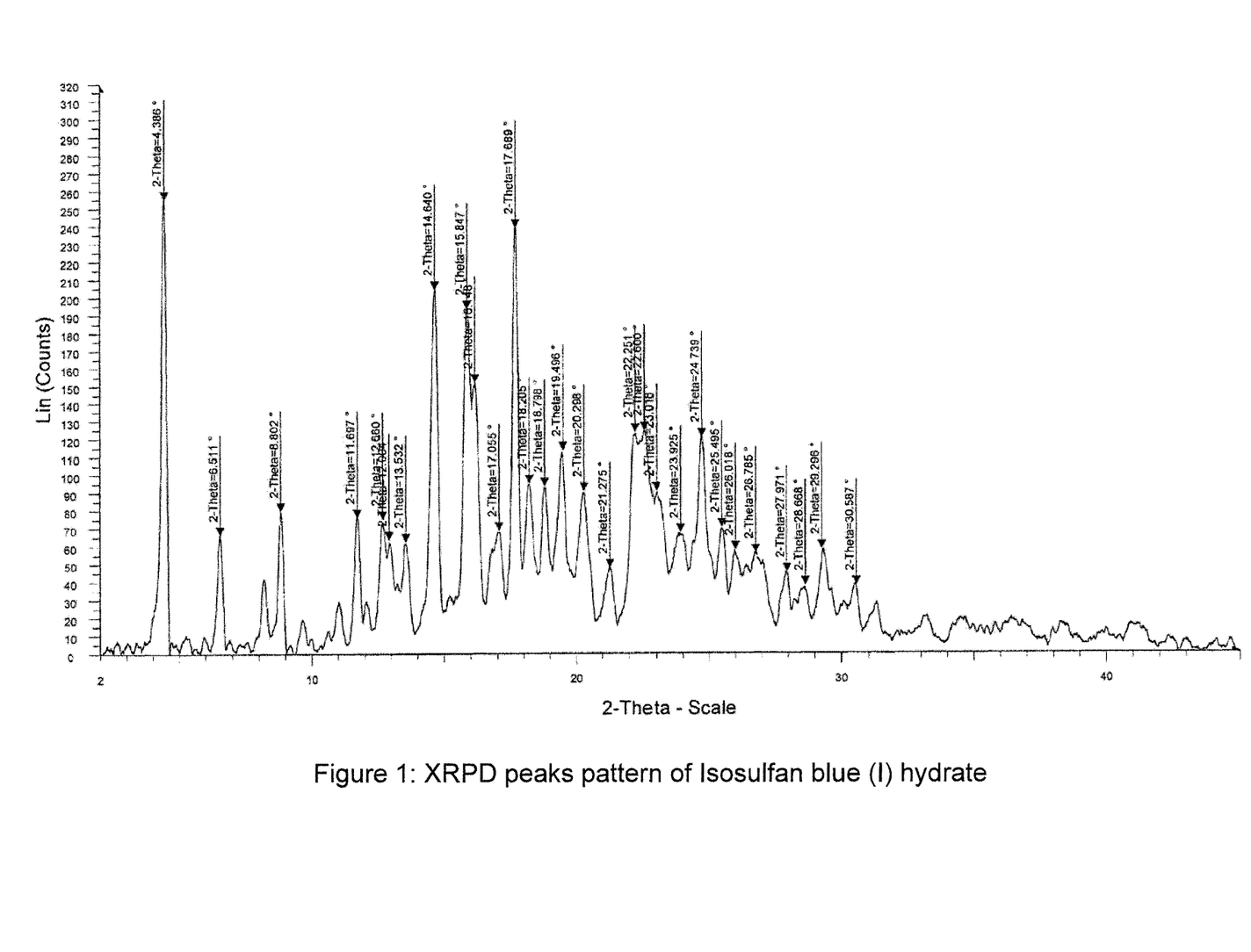
FIG. 1: Represents characteristic X-ray powder diffraction (XRPD) pattern of crystalline form of Isosulfan blue (I) hydrate.
Figure 2:
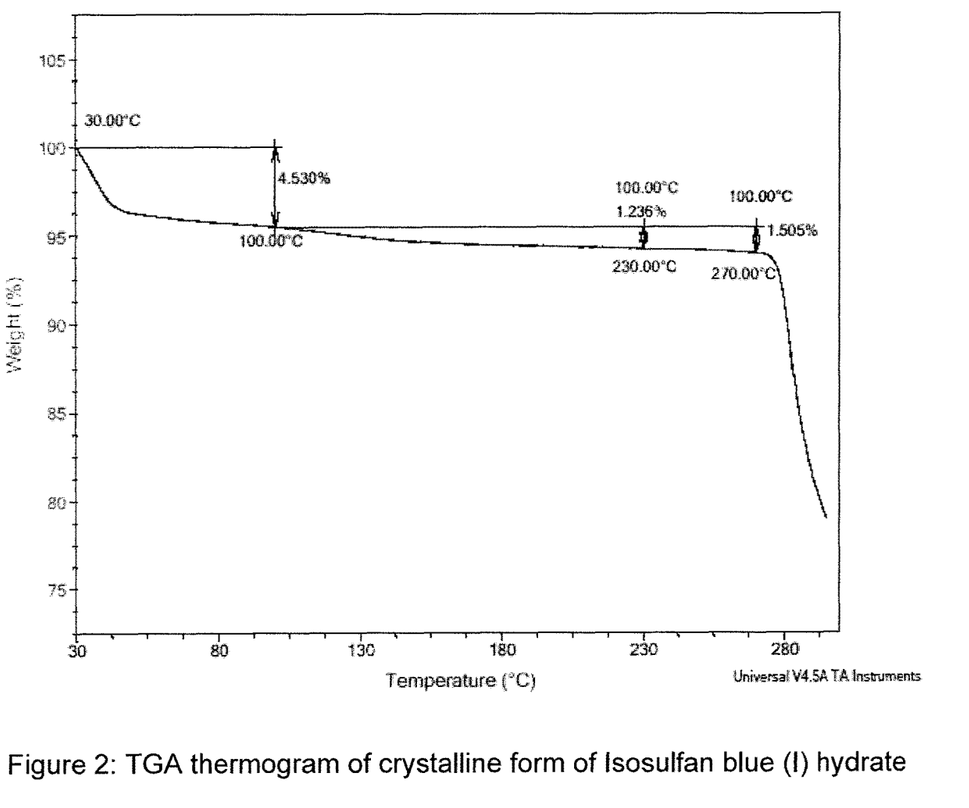
FIG. 2: Represents characteristic TGA thermogram of crystalline form of Isosulfan blue (I) hydrate.

The above said crystalline Isosulfan blue hydrate is characterized by XRPD peaks pattern as represented in FIG. 1, XRPD peaks data as presented in table-1 and TGA thermogram as represented in FIG. 2.

The above said process is further described in details in the description along with examples.

BRIEF DESCRIPTION

Some of the embodiments will be described in detail, with references to the following Figures, wherein like designations denote like members, wherein.

DETAILED DESCRIPTION

The following relates to an improved process for the preparation of Isosulfan blue of formula I in significantly In one aspect embodiments of the present invention provides a process for preparation of N-[4-[[4-(diethyl amino) phenyl](2,5-disulfophenyl)methylene]-2,5-cyclohexadien-1-ylidene]-N-ethylethanaminium inner salt sodium salt (Isosulfan Blue) of formula I comprising the steps of:

(a) sulphonation of Orthochloro benzaldehyde compound of formula II using fuming sulphuirc acid (Oleum) to obtain 4-chloro-3-formylbenzenesulfonic acid compound of formula III;

(b) conversion of 4-Chloro-3-formyl-benzenesulphonic acid compound of formula III to 1-formyl benzene-2, 5-disulphonic acid disodium salt compound of formula IV by treatment with alkali metal sulphite;

Formula IV (c) condensation of 1-formyl benzene-2,5-disulphonic acid disodium salt compound of formula IV with N,N-diethyl aniline of formula V in presence of hydrochloric acid to obtain a 4-[Bis[4-(diethylamino)phenyl]methyl]benzene-2,5-disulphonic acid compound of formula VI; optionally purifying the crude intermediate from a mixture of solvents;

Formula V

Formula VI (d) oxidizing 4-[Bis[4-(diethylamino) phenyl]methyl] benzene-2,5-disulphonic acid of formula VI with a suitable oxidizing agent in presence of inorganic acid to obtain Isosulfan blue of formula VII; optionally purifying crude compound by column chromatography;

Formula VII (e) optionally purifying the crude Isosulfan blue of formula VII by recrystallizing from suitable solvents to provide highly pure Isosulfan blue of formula I.

Formula I

Wherein, in step a) 20-25% of fuming sulphuric acid is used as a sulphonating agent and the sulphonating reaction was carried out at 1.4 equivalents of 20-25% fuming sulphuric acid.

In step b) the suitable reagent alkali metal sulphite is selected from the group comprising sodium sulphite, potassium sulphite, Iron sulphite, zinc sulphite, copper sulphite, or the like; in one embodiment the alkali metal sulphite used is sodium sulphite. The solvent is selected from alcohols comprising ethanol, methanol, propanol, isopropanol and water or mixtures thereof.

In step c) the reaction was carried out with 0.7 to 1.0 V of N,N-diethyl aniline in presence of hydrochloric acid.

In step d) the suitable oxidizing reagent is either potassium dichromate or sodium dichromate or zinc dichromate or pyridinium dichromate; the suitable acid used is sulphuric acid; suitable solvents used for the purification of Isosulfan blue crude is selected from the group methanol, acetone, dichloromethane, or the mixture thereof.

In step e) Isosulfan blue obtained in the above process is further purified from the solvents selected from group comprising alcohols like methanol, ethanol, isopropyl alcohol; water; acetonitrile; tetrahydrofuran; acetone; ethyl acetate; dichloromethane or mixtures thereof.

A preferred embodiment of the present invention provides a process for the preparation of Isosulfan blue of formula I, comprising the steps of:
(a) sulphonating Orthochloro benzaldehyde compound of formula II with 1.4 equivalents of 20-25% Oleum at 10-15° C. to obtain 4-Chloro-3-formyl-benzenesulphonic acid of formula III;
(b) conversion of 4-Chloro-3-formyl-benzenesulphonic acid of formula III to 1-formyl benzene-2,5-disulphonic acid disodium salt of formula IV by treatment with sodium sulphite and sodium hydroxide at temperature ranging 85-110° C.;
(c) condensation of 1-formyl-benzene-2,5-disulphonic acid disodium salt of formula IV with N,N-diethyl aniline of formula V in presence of hydrochloric acid to obtain a 4-[Bis[4-(diethylamino)phenyl]methyl]benzene-2,5-disulphonic acid of formula VI; optionally the obtained product is further purified by treatment with base followed by converting into free base to get pure compound VI;
(d) oxidation of 4-[Bis[4-(diethylamino) phenyl]methyl] benzene-2,5-disulphonic acid of formula VI using potassium dichromate in presence of sulphuric acid and solvent to obtain Isosulfan blue of formula VII; optionally the obtained crude is further purified by Column chromatography using dichloromethane and methanol to obtain pure Isosulfan blue;

(e) The final step involves optional purification of compound of formula VII by recrystallizing from methanol and Isopropyl alcohol to provide highly pure Isosulfan blue of formula I.

In one aspect embodiments of the present invention provides a purification process to produce of Isosulfan blue devoid of the below impurity identified at RRT 0.9 by HPLC analysis.

Formula A

Desethyl impurity (RRT: 0.9 in HPLC)

Figure 3:
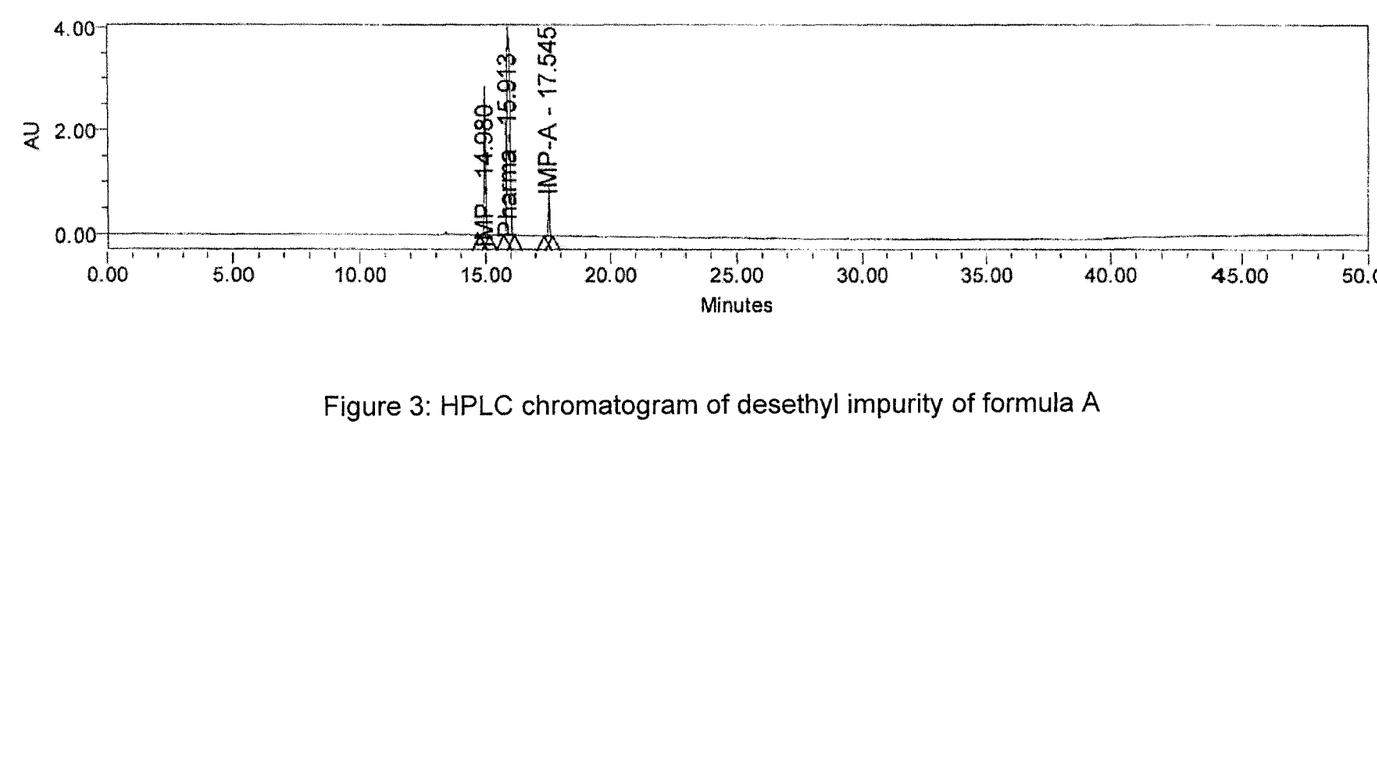
FIG. 3: Represents HPLC chromatogram of desethyl impurity of formula A.

The HPLC chromatogram of desethyl impurity of formula A is represented in FIG. 3.

In another aspect Isosulfan blue obtained in embodiments of the present invention is having desmethyl impurity of formula A level less than 0.2% and also below 0.1%. Another aspect of embodiments of the invention pertains to method of purification of Isosulfan blue to control desethyl impurity at RRT 0.9 (HPLC) by column chromatography.

The purification is carried out using 100-500 (like 100-200 or 200-400 or 230-400 or 200-425) mesh silica gel and an eluent is selected from the solvent from polar aprotic solvent such as dichloromethane, acetonitrile, methanol, ethanol and the mixtures thereof.

Optionally Isosulfan blue obtained in the above column purification is further purified to remove other process related impurities as described herein.

Isosulfan blue thus obtained in the above process is further purified by slurring in acetone followed by recrystallization from the mixture of polar protic solvents.

In one aspect polar protic solvents used for the purification of Isosulfan blue after column is selected from methanol, ethanol, propanol, isopropyl alcohol and tertiary butyl alcohol.

Embodiments of the present invention provides a process for the purification of Isosulfan blue comprising the steps of;
(a) suspending crude Isosulfan blue in suitable solvents like methanol, ethanol, isopropanol, n-butanol, acetone, diethyl ether, Isopropyl ether, dichloromethane, acetonitrile, acetic acid and tetrahydrofuran, toluene, cyclohexane solvents or mixtures thereof;
(b) stirring the solution for 1-2 hrs at 25-30° C.;
(c) filtering the solution mass through 0.2-micron filter at 25-30° C.;
(d) distilling off the filtrate under vacuum below 50° C.;
(e) cooling the crude to 25-30° C. and adding solvents like methanol, ethanol, isopropyl alcohol, n-butanol, acetone, diethyl ether, isopropyl ether at 25-30° C.;
(f) stirring for 2-3 hrs at 25-30° C.;
(g) filtering the solid under vacuum at below 30° C.; and
(h) drying the solid under vacuum below 50° C.

Isosulfan blue obtained by the above purification is having moisture content less than 10%.

Isosulfan blue obtained by the above purification is having moisture content less than 8%.

Isosulfan blue obtained by the above purification is having moisture content less than 6%.

Isosulfan blue obtained by the above purification is having moisture content less than 4%.

The preparation or purification process of embodiments of the present invention provides Isosulfan blue of formula I, which comprises metal contents i.e lead level less than 2 ppm, arsenic level less than 3 ppm and chromium level less than 50 ppm.

The process of embodiments of the present invention is the only one which gives Isosulfan blue sodium comprising impurity level less than 3% organic impurities, less than 2% impurities and less than 1% of impurities and total metal impurities less than 20 ppm.

Isosulfan blue obtained by the purification process of embodiments of the present invention is having purity of greater than 98%, greater than 99% and desethyl impurity less than 0.2% and also less than 0.1%.

The present inventors also found that the crystalline form of Isosulfan blue exists as further hydrated forms by exposing Isosulfan blue sodium at ambient temperature having a relative humidity 50-75% with increase in the moisture content from 10 to 15%. Ambient temperature means a temperature from 15 to 30° C., also from 25 to 30° C.

In one embodiment of the invention Isosulfan blue obtained in the above process is crystalline form of Isosulfan blue hydrate.

In one aspect of the invention, a crystalline polymorphic form of Isosulfan blue hydrate is reported, whose X-ray powder diffraction (XRPD) pattern is represented by FIG. 1 and XPRD values are tabulated in Table 1.

The crystalline polymorphic form of Isosulfan blue hydrate may produce an X-ray diffraction pattern comprising one or more of the following reflections at 4.38, 14.64, 15.84, 16.14, 19.49, 22.25, 22.60, 24.73±0.2 degrees 2 theta (2θ°) or that produces an X-ray powder diffraction pattern further comprising one or more of the following reflections at 6.51, 8.80, 11.69, 12.66, 12.90, 13.53, 17.05, 18.20, 18.79, 20.29, 21.27, 23.01, 23.92, 25.49, 26.01, 26.78, 27.97, 28.66, 29.29 and 30.58±0.2 degrees 2 theta (2θ°) or that produces an X-ray powder diffraction pattern comprising the 2 theta values as tabulated in Table-1.

The crystalline polymorphic form of Isosulfan blue hydrate may also be identified by the TGA thermogram as depicted in FIG. 2.

Isosulfan blue obtained by the process of embodiments of the present invention is analysed by TGA and XRPD. The XRPD data of the crystalline form of Isosulfan blue hydrate obtained is tabulated in below table-1:

TABLE 1

X-Ray powder diffraction (XRPD) data of crystalline polymorphic form of Isosulfan blue hydrate

| S. No. | 2 Theta° | d value Angstrom | Relative intensity % |
|---|---|---|---|
| 1. | 4.38 | 20.12 | 100 |
| 2. | 6.51 | 13.56 | 25.9 |
| 3. | 8.80 | 10.03 | 31.2 |
| 4. | 11.69 | 7.55 | 29.8 |
| 5. | 12.66 | 6.98 | 29.4 |
| 6. | 12.90 | 6.85 | 24.8 |

TABLE 1-continued

X-Ray powder diffraction (XRPD) data of crystalline polymorphic form of Isosulfan blue hydrate

| S. No. | 2 Theta° | d value Angstrom | Relative intensity % |
|---|---|---|---|
| 7. | 13.53 | 6.53 | 24.4 |
| 8. | 14.64 | 6.04 | 80.2 |
| 9. | 15.84 | 5.58 | 76 |
| 10. | 16.14 | 5.48 | 59.7 |
| 11. | 17.05 | 5.19 | 26.9 |
| 12. | 17.68 | 5.00 | 94 |
| 13. | 18.20 | 4.86 | 37.4 |
| 14. | 18.79 | 4.71 | 36.8 |
| 15. | 19.49 | 4.54 | 44.7 |
| 16. | 20.29 | 4.37 | 35.7 |
| 17. | 21.27 | 4.17 | 18.7 |
| 18. | 22.25 | 3.99 | 48.7 |
| 19. | 22.6 | 3.93 | 49 |
| 20. | 23.01 | 3.86 | 35.9 |
| 21. | 23.92 | 3.71 | 26.5 |
| 22. | 24.73 | 3.59 | 47.6 |
| 23. | 25.49 | 3.49 | 27.7 |
| 24. | 26.01 | 3.42 | 22.7 |
| 25. | 26.78 | 3.32 | 21.9 |
| 26. | 27.97 | 3.18 | 17.7 |
| 27. | 28.66 | 3.11 | 14.9 |
| 28. | 29.29 | 3.04 | 22.9 |
| 29. | 30.58 | 2.92 | 14.9 |

The following examples further illustrate embodiments of the present invention, but should not be construed in any way as to limit its scope.

Example 1: Preparation of 4-Chloro-3-Formyl-Benzenesulfonic Acid of Formula III 2-chlorobenzaldehyde
Formula II 4-chloro-3-formylbenzenesulfonic acid
Formula III 100 g of 2-chlorobenzaldehyde was charged to 4 volumes of 20-25% of fuming sulphuric acid over a period of 1-2 hrs at 10-15° C. stirred the reaction mass temperature for 30-40 minutes at 10-15 and gradually raised the temperature to 25-30° C. and then to 65-70° C. The obtained reaction mass was further stirred for 5-6 hrs at 65-70° C. and quenched in cold water. To this 300 g of sodium chloride was added and stirred for 3-4 hrs at 25-30° C. Filtered the precipitated solid and dried under vacuum at below 75° C. Yield: 50% Purity: NLT 95%

Example 2: Preparation of Sodium 2-Formylbenzene-1,4-Disulfonate

Formula III
4-chloro-3-formylbenzenesulfonic acid

Formula IV
Sodium 2-formylbenzene-1,4-disulfonate 10 g of 4-Chloro-3-formyl-benzenesulfonic acid was dissolved in 25 ml of water and adjusted pH of the reaction mass to 9-10.5 with aqueous Sodium hydroxide solution. To this, 2.3 g of Sodium sulphite and 4 ml of water were added and heated to 100-105° C. Stirred the reaction mass for 12-14 hrs at 100-105° C. Water was distilled off and the residue was stripped off with 20 ml of Isopropyl alcohol. The reaction mixture was stirred in 300 ml of Isopropyl alcohol at 20-30 min, then cooled to 10-15° C., stirred for 1 hr, filtered, washed with of Isopropyl alcohol and dried under vacuum at temperature below 50° C. to get Sodium 2-formylbenzene-1,4-disulfonate. Purity: NLT 85%

Example 3: Preparation of 2-(Bis(4-(Diethylamino)Phenyl)Methyl)Benzene-1,4-Disulfonic Acid

Formula IV
Sodium 2-formylbenzene-1,4-disulfonate

Formula VI
2-(bis(4-(diethylamino)phenyl)methyl)benzene-1,4-disulfonic acid 90 ml of N,N-diethyl aniline was added to 100 g of Sodium2-formylbenzene-1,4-disulfonate at 25-30° C. To this 33-66 ml of Concentrated Hydrochloric acid was added over a period of 20-30 min. The reaction mixture was heated to 100-105° C. and maintained for 12-14 hrs. After reaction completion, cooled to 25-30° C. then to 0-5° C. Charged 50 ml of Isopropyl alcohol, stirred for 20-30 min, filtered and washed with chilled (0-5° C.) Isopropyl alcohol. Slurried above solid in Isopropyl alcohol and added 400 ml of Ethanol and cooled to 0-5° C. The pH was adjusted between 11.5-12.0 using aqueous Sodium hydroxide solution, stirred for 1 hr, filtered and washed with 200 ml of chilled (0-5° C.) Ethanol. Distilled off the filtrate and charged 100 ml of water and cooled to 0-5° C. The pH was adjusted between 1-2 using conc. Hydrochloric acid and maintained for 4-5 hrs, filtered, washed with 200 ml chilled water and dried under vacuum at temperature below 60° C. to get 2-(Bis(4-(diethylamino)phenyl)methyl)benzene-1,4-disulfonic acid of formula VI. PurityNLT 96%; Yield 25%

Example 4: Preparation of Isosulfan Blue Using Potassium Dichromate as Oxidizing Agent

Formula VI
2-(Bis(4-(diethylamino)phenyl)methyl)benzene-1,4-disulfonic acid Formula VII
N-[4-[[4-(Diethyl amino) phenyl](2,5-disulfophenyl)methylene]-2,5-cyclohexadien-1-ylidene]-N-ethylethanamimium inner salt sodium salt To 100 g of 2-(Bis(4-(diethylamino)phenyl)methyl)benzene-1,4-disulfonic acid, 50 ml of methanol, 100 ml of water and 15 g of Sodium hydroxide were added at 25-30° C. Cooled to 0-5° C., 25 g of Potassium dichromate was added over a period of 20-30 min, stirred for 15-20 min, 200 ml of 25% aqueous sulphuric acid solution was added over a period of 30-40 min. The reaction mixture temperature was raised to 25-30° C., stirred for 10-12 hrs and charged 500 ml of water, cooled the reaction mixture to 0-5° C. and adjusted pH of the reaction mass between 8.5-9.0 using 600 ml of aqueous sodium hydroxide solution, 25 g of potassium dichromate was added over a period of 20-30 min, stirred for 15-20 min, 200 ml of aqueous 25% sulphuric acid solution was added over a period of 20-30 min. The reaction mixture temperature was raised to 25-30° C. and stirred for 4-5 hrs. After reaction completion, cooled to 0-5° C., pH was adjusted between 9.5-10.0 using 300 ml of 20% aqueous Sodium hydroxide solution. The reaction mixture temperature was raised to 25-30° C. and stirred for 60-90 min, filtered through hyflo and washed with methanol. Filtrate was distilled off under vacuum below 70° C., then charged 1000 ml of ethanol. Stirred the reaction mass for 20-30 min, filtered and washed with chilled (0-5° C.) ethanol followed by chilled (0-5° C.) methanol.

Purification of Isosulfan blue to remove desethyl impurity: Filtrate was distilled off to half of its total volume at below 65° C., cooled to 25-30° C., the obtained crude (purity~65%) was impregnated with 500 g of (230-400 mesh) Silica gel and dried at NMT 55° C. Column was packed with (230-400 mesh) Silica gel and loaded the impregnated crude, eluted the column using dichloromethane and methanol gradient mixture as eluent. Compound was eluted in 8-12% of methanol in dichloromethane, collected the fractions distilled off the solvent from pure fractions under vacuum at 40° C. The obtained crude was slurred in acetone for 1 hr, filtered and washed with acetone. The obtained compound was dried under vacuum below 50 to get Isosulfan blue sodium. Purity NLT 98%; yield 30%.

Example 5: Purification of Isosulfan Blue (I)

Formula VII
N-[4-[[4-(Diethyl amino) phenyl](2,5-disulfophenyl)methylene]-2,5-cyclohexadien-1-ylidene]-N-ethylethanamimium inner salt sodium salt Formula I
N-[4-[[4-(Diethyl amino) phenyl](2,5-disulfophenyl)methylene]-2,5-cyclohexadien-1-ylidene]-N-ethylethanamimium inner salt sodium salt To a 30 g of Isosulfan blue sodium, 300 ml of methanol was added and stirred for 1 hr at 25-30° C. Filtered the reaction mixture through 0.2 μ micron filter and distilled off the solvent under vacuum below 50° C. Cooled the crude mass to 25-30° C. and stirred for 2-3 hrs in Isopropyl alcohol. Filtered and dried the solid below 50° C. to get Isosulfan blue sodium. Purity NLT 99.9%; yield 90%.

We claim:
1. A hydrate of Isosulfan blue sodium of formula I

(I)

comprising metal impurities of lead, arsenic and chromium, wherein lead is present at less than 2 ppm, arsenic is present at less than 3 ppm, and chromium is present at less than 50 ppm.

2. A Crystalline Isosulfan blue hydrate characterized by X-ray powder diffraction (XRPD) pattern comprising one or more of the reflections at 4.38, 14.64, 15.84, 16.14, 19.49, 22.25, 22.60 and 24.73±0.2 degrees 2 theta (2θ°).

3. The crystalline Isosulfan blue hydrate as claimed in claim 2, further characterized by X-ray powder diffraction (XRPD) pattern comprising of the reflections at 6.51, 8.80, 11.69, 12.66, 12.90, 13.53, 17.05, 17.68, 18.20, 18.79, 20.29, 21.27, 23.01, 23.92, 25.49, 26.01, 26.78, 27.97, 28.66, 29.29 and 30.58±0.2 degrees 2 theta (2θ°).

* * * * *